US010702713B2

(12) United States Patent
Mori et al.

(10) Patent No.: US 10,702,713 B2
(45) Date of Patent: Jul. 7, 2020

(54) X-RAY FLUOROSCOPIC APPARATUS

(71) Applicant: SHIMADZU CORPORATION, Nakagyo-Ku, Kyoto-Shi, Kyoto (JP)

(72) Inventors: Shinichiro Mori, Chiba (JP); Wataru Takahashi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 15/497,263

(22) Filed: Apr. 26, 2017

(65) Prior Publication Data

US 2018/0154180 A1 Jun. 7, 2018

(30) Foreign Application Priority Data

Dec. 1, 2016 (JP) ................................ 2016-233960

(51) Int. Cl.

| | |
|---|---|
| ***A61N 5/10*** | (2006.01) |
| ***A61B 6/00*** | (2006.01) |
| ***G21K 4/00*** | (2006.01) |

(52) U.S. Cl.

CPC .......... *A61N 5/1049* (2013.01); *A61B 6/4266* (2013.01); *A61B 6/487* (2013.01); *G21K 4/00* (2013.01); *A61N 5/1068* (2013.01); *A61N 2005/1061* (2013.01); *A61N 2005/1062* (2013.01)

(58) Field of Classification Search

CPC ................ A61N 5/1049; A61N 5/1068; A61N 2005/1061; A61N 2005/1062; A61B 6/4266; A61B 6/487; G21K 4/00

USPC ............................................. 378/41, 42, 44

See application file for complete search history.

(56) References Cited

U.S. PATENT DOCUMENTS

| | | | |
|---|---|---|---|
| 2011/0249797 | A1 | 10/2011 | Terunuma et al. |
| 2017/0043184 | A1 | 1/2017 | Mori et al. |

FOREIGN PATENT DOCUMENTS

| | | |
|---|---|---|
| JP | 2016-106756 | 6/1916 |
| JP | 3053389 | 4/2000 |
| JP | 2009-95644 | 5/2009 |
| JP | 2010-069086 | 4/2010 |
| JP | 2010-89086 | 4/2010 |
| JP | 2015-54133 | 3/2015 |
| WO | WO 2010/055881 | 5/2010 |
| WO | WO 2015/125600 | 8/2015 |

OTHER PUBLICATIONS

JP 2016-233960, Notice of Reasons for Refusal dated Feb. 25, 2020, 4 pages—Japanese, 4 pages—English.

*Primary Examiner* — Courtney D Thomas

(74) *Attorney, Agent, or Firm* — Lackenbach Siegel, LLP; Andrew F. Young, Esq.

(57) ABSTRACT

An X-ray fluoroscopic apparatus is capable of irradiating exactly a therapeutic beam considering a specific-regional area, and in addition is able to perform an easy confirmation of the specific region even when the specific region is difficult to visually recognize by a user. A control element 30 has a DRR image generation element 31, an X-ray fluoroscopic radiograph generation element 32, a template area selection element 33, a template generation element 34, a position detection element 35, a radiation area projection element 36, a specific region projection element 37, a superimposition element 38, an image display element 39, a gating element 40 and a memory storing element 41 that stores a variety of data including image data.

12 Claims, 6 Drawing Sheets

21b
21a
93
90
92
91
11b
29
11a

Control Element 30
DRR Image Generation Element 31
X-ray Fluoroscopic Radiograph Generation Element 32
Template Area Selection Element 33
Template Generation Element 34
Position Detection Element 35
Irradiation Area Projection Element 36
Specific Region Projection Element 37
Superimposition Element 38
Image Display Element 39
Gating Element 40
Memory Storing Element 41
11a First X-ray Tube
11b Second X-ray tube
21a First FPD
21b Second FPD
42 Display Element
90 Radiation Irradiation Device
99 Therapy Planning Device

X-RAY FLUOROSCOPIC APPARATUS

CROSS REFERENCE TO RELATED APPLICATIONS

This application relates to, and claims priority from, Ser. No. JP 2016-233960 filed Dec. 1, 2016, the entire contents of which are incorporated herein by reference.

BACKGROUND OF THE INVENTION

Field of the Invention

The present invention relates to an X-ray fluoroscopic apparatus to obtain an image including a specific region of a subject by detecting an X-ray, which is irradiated from the X-ray tube and passes through the subject, by an X-ray detector, and particularly detect a position of the specific region from the image including the specific region of the subject and track the movement of the specific region.

Description of the Related Art

The radiation relative to a radiation therapy, in which the radiation including an X-ray and an electron beam and so forth is irradiated to an affected area including tumor and so forth, must be accurately irradiated to the affected area. Nevertheless, in some cases, not only the subject unintentionally may move the body thereof, but also the affected area per se may move. For example, a tumor near the lung largely moves depending on breathing. Accordingly, a radiation irradiation device of marker tracking method having an aspect, in which the irradiation timing of the therapeutic beam is controlled while detecting the position of the spherical metal marker embedded near a tumor by an X-ray fluoroscopic device, is disclosed (referring to Patent Document 1).

According to such radiation irradiation device, the marker embedded inside the body is radiographed using a first X-ray fluoroscopic mechanism comprising a first X-ray tube and a first X-ray detector and the second X-ray fluoroscopic device mechanism comprising a second X-ray tube and a second X-ray detector and a three-dimensional positional data is obtained utilizing the two-dimensional fluoroscopic radiograph provided by the first X-ray fluoroscopic mechanism and the two-dimensional fluoroscopic radiograph provided by the second X-ray fluoroscopic mechanism. Subsequently, the marker of the region accompanying movement can be detected with a high degree of accuracy by continuously performing the X-ray fluoroscopy and calculating the real-time three-dimensional positional data of the marker. And an irradiation timing of the therapeutic beam is controlled based on the positional data of the detected marker, so that the radiation irradiation of the radiation corresponding to movement of the tumor can be performed with a high degree of accuracy. When the positional data of the marker is obtained, a template matching utilizing a template is executed.

Meantime, a marker must be embedded in advance inside the body of the subject to detect the movement of the tumor utilizing the marker set forth above. On the other hand, recently a markerless (non-marker) tracking without embedding the marker is proposed, in which a specific region such as the patient's tumor area is used instead of the marker.

RELATED PRIOR ART DOCUMENTS

Patent Document

Patent Document 1: JP Patent 3053389 B1

ASPECTS AND SUMMARY OF THE INVENTION

Objects to be Solved

When the marker tracking method is adopted, the marker is tracked as a point, but when the markerless tracking is adopted, the specific region per se having a predetermined size is being tracked. Nevertheless, according to the conventional tracking method, for example, a position (location) of any one point of the specific region such as center of the specific region is calculated and a specific-regional area is not directly considered. In contrast, since the region to which the therapeutic beam is irradiated is registered as the area having a constant size, it is desirable that the specific-regional area should also be considered.

In addition, relative to the marker tracking using the template matching, a template is generated by selecting the marker which is visually recognizable in a high level. On the other hand, relative to markerless tracking, a template is generated by selecting the position of the specific region. However, in many cases, the specific region in the fluoroscopic radiograph is poorly recognizable and particularly, in many cases, the border of the specific region is hardly recognizable. In such case, it is difficult to select the accurate position of the specific region and the template may be generated by selecting an off-position of the specific region. In such case, it is problematic that the accuracy degree of the template matching decreases.

In addition, when to select the specific region, a user designates manually the position thereof while watching the X-ray fluoroscopic radiograph, but many hours are required to generate the template because many templates must be generated to perform an accurate template matching. Consequently, not only it is painful for the patient restrained to the examination table (couch) and waiting for generation thereof, but also it is problematic that the therapeutic throughput decreases.

Further, even when other tracking method such as a machine learning and so forth instead of a template matching for tracking the specific region is used; when the operator confirms the tracking of the specific region right before the therapy or monitors during the therapy, it is problematic that it is difficult for the operator to realize whether or not the specific region is being tracked correctly because the specific region is poorly recognizable by eyes.

The present invention is intended to solve such problems described above and the purpose of the present invention is to provide an X-ray fluoroscopic apparatus capable of irradiating exactly the therapeutic beam under consideration of the specific-regional area, and in addition, preferably capable of performing easily confirmation of the specific region even when the specific region is poorly recognizable by eyes.

Means for Solving the Problem

According to the first invention, an X-ray fluoroscopic apparatus comprises: an X-ray tube; and an X-ray detector that detects the X-ray which is irradiated from the X-ray tube and transmits through the subject; wherein the X-ray fluoroscopic apparatus collects a X-ray fluoroscopic radiograph including a specific region of the subject and detects a position of the specific region, and sends a therapeutic beam irradiation signal to a radiation irradiation device while tracking a movement of the specific region; and further comprises: an irradiation area projection element that generates a projection area denoting the therapeutic beam irradiation area by performing a virtual fluoroscopic projection simulating a geometric fluoroscopic condition between the X-ray tube and the X-ray detector relative to CT image data based on the therapeutic beam irradiation area registered in the CT image data of the subject generated when a therapy planning is created; a specific region projection element that generates a projection area denoting the specific-regional area by performing a virtual fluoroscopic projection simulating a geometric fluoroscopic condition between the X-ray tube and the X-ray detector relative to CT image data of the subject based on the specific region registered on the CT image data of the subject generated when a therapy planning is created; a superimposition element that not only superimposes the projection area denoting the therapeutic beam irradiation area to the X-ray fluoroscopic radiograph, but also superimposes the projection area denoting the specific-regional area to the X-ray fluoroscopic radiograph at the specific-regional position detected based on the X-ray fluoroscopic radiograph; a gating element that sends the therapeutic beam irradiation signal to the radiation irradiation apparatus when the projection area denoting the specific-regional area superimposed to the X-ray fluoroscopic radiograph by said superimposition element are placed in the projection area denoting the therapeutic beam irradiation area superimposed to the X-ray fluoroscopic radiograph by the superimposition element.

According to the second invention, an X-ray fluoroscopic apparatus comprises: an image display element that displays not only X-ray fluoroscopic radiograph, but also the projection area denoting the therapeutic beam irradiation area superimposed to the X-ray fluoroscopic radiograph by the superimposition element and the projection area denoting the area of the specific region superimposed to the X-ray fluoroscopic radiograph by the superimposition element.

According to the third invention, an X-ray fluoroscopic apparatus comprises: a template area selection element that selects an area including the specific region from the X-ray fluoroscopic radiograph; a template generation element that generates a template indicating the specific region from an area including said specific region selected by the template area selection element; a position detection element that detects a position of the specific region relative to the fluoroscopic radiograph by performing template matching by using the X-ray fluoroscopic radiograph and a template generated by the template generation element.

According to an aspect of the fourth invention, the template area selection element selects the area including the specific region from the X-ray fluoroscopic radiograph by DRR (digital reconstructed radiography) image generated by performing the virtual fluoroscopic projection simulating the geometric fluoroscopic condition between the X-ray tube and the X-ray detector relative to CT image data or by machine learning learned using the X-ray fluoroscopic radiograph obtained by X-ray fluoroscopy of the subject in advance.

According to an aspect of the fifth invention, the machine learning is one selected from the group consisting of a support vector machine, a decision tree, a boosting and a neural network.

According to the six invention, an X-ray fluoroscopic apparatus comprises: a DRR image generation element that generates a DRR image including the specific region by performing a virtual fluoroscopic projection simulating a geometric fluoroscopic condition between the X-ray tube and the X-ray detector relative to CT image data of the subject generated when a therapy planning is created; and an image display element that displays an image including the specific region selected by the template area selection element and an image obtained by superimposing a projection area denoting the specific region generated by the specific region projection element to a DRR image generated by the DRR image generation element.

According to the aspect of the seventh invention, a DRR image generation element that generates a DRR image including the specific region by performing a virtual fluoroscopic projection simulating a geometric fluoroscopic condition between the X-ray tube and the X-ray detector relative to CT image data of the subject generated when a therapy planning is created; and an image display element that displays the X-ray fluoroscopic radiograph and an image obtained by superimposing a projection area denoting the specific region generated by the specific region projection element to a DRR image generated by the DRR image generation element.

According to the aspect of the eighth invention, the CT image data is a 4-dimensional CT image data comprising a group of 3-dimensional CT image data including the specific region relative to a plurality of continuous breathing phases of the subject and the DRR image generation element generates the DRR image including specific region based on the CT image data of the phases in association with the X-ray fluoroscopic radiograph.

According to the aspect of the ninth invention, the CT image data is a 4-dimensional CT image data comprising a group of 3-dimensional CT image data including the specific region relative to a plurality of continuous breathing phases of the subject and the specific region projection element that generates the projection area denoting the specific region based on the CT image data of the phases in association with the X-ray fluoroscopic radiograph.

According to the tenth invention, an X-ray fluoroscopic apparatus comprises: an X-ray tube; and an X-ray detector that detects the X-ray which is irradiated from the X-ray tube and transmits through the subject; wherein the X-ray fluoroscopic apparatus collects a X-ray fluoroscopic radiograph including a specific region of the subject and detects a position of the specific region, and sends a therapeutic beam irradiation signal to a radiation irradiation device while tracking a movement of the specific region; and further comprises: a specific region projection element that generates a projection area denoting the specific-regional area by performing a virtual fluoroscopic projection simulating a geometric fluoroscopic condition between the X-ray tube and the X-ray detector relative to CT image data of the subject based on the specific region registered on the CT image data of the subject generated when a therapy planning is created; a DRR image generation element that generates a DRR image including the specific region by performing a virtual fluoroscopic projection simulating a geometric fluoroscopic condition between the X-ray tube and the X-ray detector relative to CT image data of the subject generated when the therapy planning is created; a template area selection element that selects the area including the specific region from the X-ray fluoroscopic radiograph; an image display element that displays the image of the area including the specific region in the X-ray fluoroscopic radiograph selected by the template area selection element and the image obtained by superimposing the projection area denoting the specific region generated by the specific region projection element to the DRR image generated by the DRR image generation element a template generation element that generates a template indicating the specific region from the area including the specific region selected by the template area selection element; a position detection element that detects a position of the the specific region relative to the fluoroscopic radiograph by performing template matching by using a template generated by the X-ray fluoroscopic radiograph and the template generation element.

According to the aspect of the eleventh invention, the template area selection element selects the area including the specific region from the X-ray fluoroscopic radiograph by DRR (digital reconstructed radiography) image generated by performing the virtual fluoroscopic projection simulating the geometric fluoroscopic condition between the X-ray tube and the X-ray detector relative to CT image data or by machine learning learned using the X-ray fluoroscopic radiograph obtained by X-ray fluoroscopy of the subject in advance.

According to the twelfth invention, the X-ray fluoroscopic apparatus comprises: the machine learning that is one selected from the group consisting of a support vector machine, a decision tree, a boosting and a neural network.

Effect of the Invention

According to the first invention, the superimposition element that not only superimposes the projection area denoting the therapeutic beam irradiation area to the X-ray fluoroscopic radiograph, but also superimposes the projection area denoting the specific-regional area to the X-ray fluoroscopic radiograph at the position detected based on the X-ray fluoroscopic radiograph, so that the therapeutic beam can be irradiated exactly considering the specific-regional area.

According to an aspect of the second invention, both projection area denoting the therapeutic beam irradiation area and the projection area denoting the specific-regional area are displayed on the display element together with the X-ray fluoroscopic radiograph, so that the specific region can be easily confirmed even when the specific region is poorly recognizable According to the third invention, the projection area denoting the specific-regional area can be superimposed to the position of the specific region detected by applying the template matching.

According to the fourth and the fifth inventions, the area including the specific region can be selected by applying the machine learning time needed to generate a template can be shortened.

According to the sixth invention, the image including the specific region and the image in which the projection area denoting the specific-regional area is superimposed to the DRR image are displayed, so that it is feasible to confirm whether or not the position of the template is appropriate by comparing both images when the template is generated even when the specific region is poorly recognizable by eyes.

According to the aspect of the seventh invention, both the X-ray fluoroscopic radiograph and the image in which the projection area denoting the specific-regional area is superimposed to the DRR image are displayed, so that it is feasible to confirm whether or not the tracking is being correctly performed by comparing both images when the tracking is ongoing, even when the specific region is poorly recognizable by eyes.

According to the aspect of the eighth invention, the four-dimensional CT data is used, so that the DRR image corresponding to the breathing (respiratory) phase of the subject can be generated.

According to an aspect of the ninth invention, the four-dimensional CT data is used, so that the projection area corresponding to the breathing (respiratory) phase of the subject can be generated.

According to an aspect of the tenth invention, the image including the specific region in the X-ray fluoroscopic radiograph and the image in which the projection area denoting the specific-regional area is superimposed to the DRR image are displayed when the template is generated, so that it is feasible to confirm whether or not the image including the selected specific region is correct even when the specific region is poorly recognizable by eyes.

According to the eleventh and twelfth inventions, the area including the specific region can be selected by applying the machine learning time needed to generate a template can be shortened.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
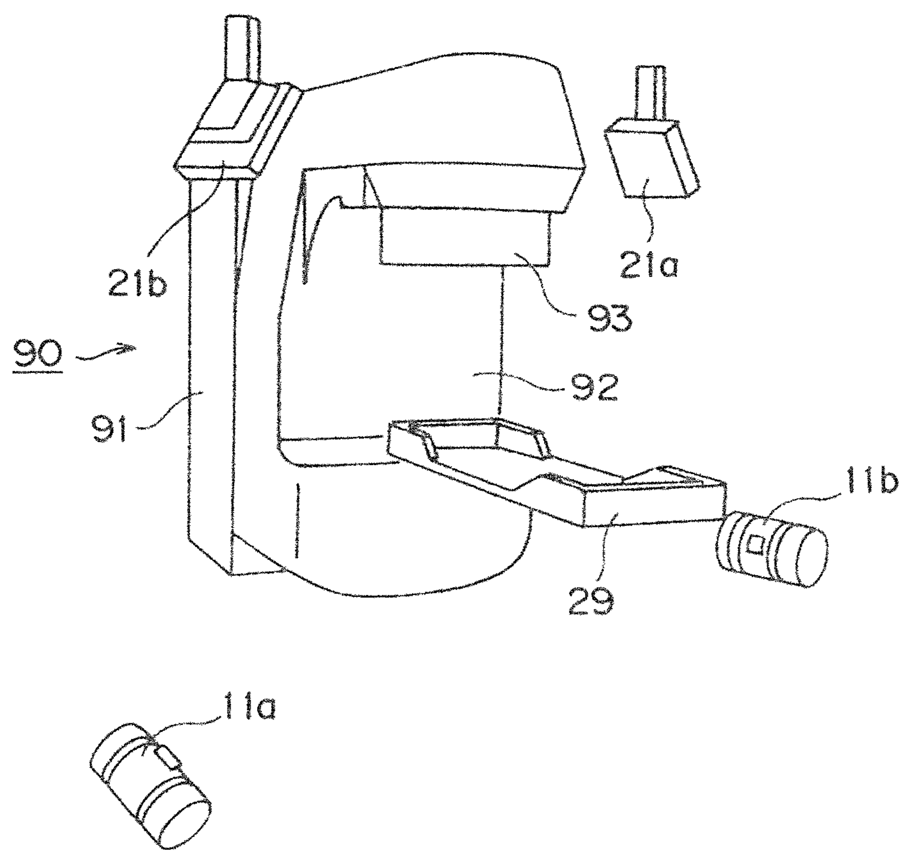
FIG. 1 is a perspective view of an X-ray fluoroscopic apparatus of the present invention together with a radiation irradiation device 90.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Such X-ray fluoroscopic apparatus comprises: a CPU as a processor that executes the logic operation; a ROM that stores operation programs required to control the apparatus; a RAM that stores temporally the data and so forth when controlling; and so forth; and further comprises: a control element 30 that controls the entire apparatus. The control element 30 is connected, as described above, to the first X-ray tube 11*a*, the second X-ray tube 11*b*, the flat panel detector 21*a* and the second flat panel detector 21*b*. In addition, the control element 30 is connected to a display element 42 consisting of the liquid crystal display panel and so forth.

The radiation irradiation device 90 irradiates radiation to a subject on the examination table 29 (also known as couch) and comprises a gantry 92 that is swingable relative to the pedestal 91 installed on the floor of the therapy room and a head 93 that emits the therapeutic beam installed to the gantry 92. Such radiation irradiation device 90 can change the irradiation direction of the therapeutic beam irradiated from the head 93 by swinging (oscillating) the gantry 92 relative to the pedestal 91. Consequently, the therapeutic beam can be irradiated from a variety of directions to the affected area such as a tumor and so forth of the subject.

The X-ray fluoroscopic apparatus used together with such radiation irradiation device 90 executes an X-ray fluoroscopy to perform a tracking to identify the position of the affected area of the subject. Specifically, when performing such radiation therapy using the radiation irradiation device 90, the radiation must be accurately irradiated to the affected area that moves along with the body movement of the subject. Therefore, the specific region is detected in a high accuracy degree by pre-registration of the region having a specific shape, such as a tumor of the subject, performing continuously an X-ray fluoroscopy and calculating the three-dimensional position data of the specific region, so that so-to-speak a tracking can be performed to detect the specific region in a high degree of accuracy. In such way, a tracking method, in which an image of the specific region such as e.g., tumor of the subject is used as a marker instead of conventionally setting the marker near the affected area of the subject, is called as a markerless tracking.

The X-ray fluoroscopic apparatus comprises a first X-ray tube 11*a* and a second X-ray tube 11*b*, and a first flat panel detector 21*a* and a second flat panel detector 21*b*. The X-ray irradiated from the first X-ray tube 11*a* transmits the subject on the examination table 29 and subsequently, is detected by the first flat panel detector 21*a*. A first X-ray radiography system comprises the first X-ray tube 11*a* and the first flat panel detector 21*a*. The X-ray irradiated from the second X-ray tube 11*b* transmits the subject on the examination table 29 and subsequently, is detected by the second flat panel detector 21*a*. A second X-ray radiography system comprises the second X-ray tube 11*b* and the second flat panel detector 21*b*.

Figure 2:
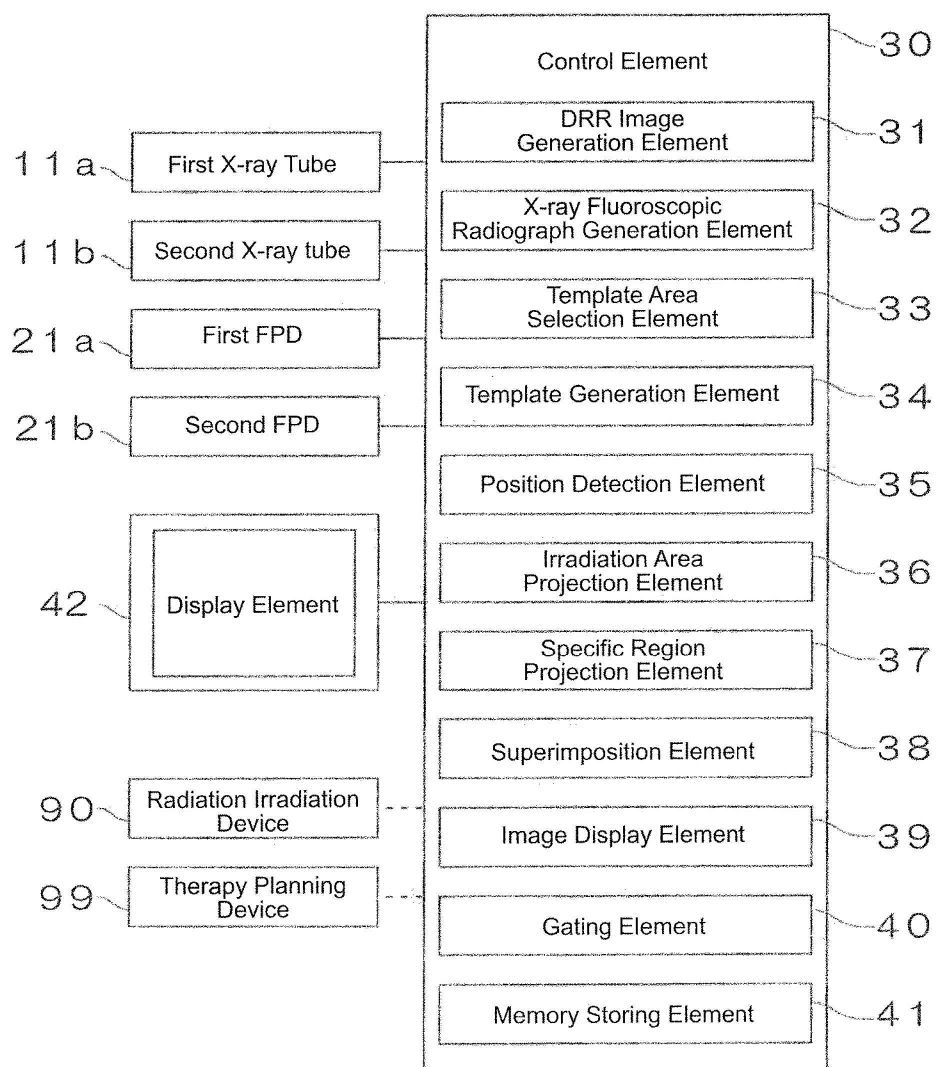
FIG. 2 is a block diagram illustrating the main control system of the X-ray fluoroscopic apparatus of the present invention.

FIG. 2 is a block diagram illustrating the main control system of the X-ray fluoroscopic device according to the aspect of the present invention.

Such X-ray fluoroscopic apparatus comprises: a CPU as a processor that executes the logic operation; a ROM that stores operation programs required to control the apparatus; a RAM that stores temporally the data and so forth when controlling; and so forth; and further comprises: a control element 30 that controls the entire apparatus. The control element 30 is connected, as described above, to the first X-ray tube 11*a*, the second X-ray tube 11*b*, the flat panel detector 21*a* and the second flat panel detector 21*b*. In addition, the control module 30 is connected to a display element 42 consisting of the liquid crystal display panel and so forth.

The control element 30 comprises, as a functional component, a DRR image generation element 31, an X-ray fluoroscopic radiograph generation element 32, a template area selection element 33, a template generation element 34, a position detection element 35, a radiation area projection element 36, a specific region projection element 37, a superimposition element 38, a image display element 39, a gating element 40 and a memory storing element 41 that stores a variety of data including image data.

The DRR image generation element 31 generates the DRR image including the specific region by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the four-dimensional CT image data, which is generated on the therapy planning, comprising a three-dimensional CT image data group consisting of the specific region in a plurality of continuous breathing phases of the subject. In addition, the X-ray fluoroscopic radiograph generation element 32 generates an X-ray fluoroscopic radiograph based on the X-ray fluoroscopy by the first X-ray radiography system comprising the first X-ray tube 11*a* and the first flat panel detector 21*a* and the second X-ray radiography system comprising the second X-ray tube 11*b* and the second flat panel detector 21*b*.

The template area selection element 33 selects an area including the specific region from the X-ray fluoroscopic radiograph when the template is generated to execute template matching. The template generation element 34 generates the template indicating the specific region from the area including the specific region selected by the template area selection element 33. Further, the position detection element 35 detects the position of the specific region relative to the fluoroscopic radiograph by performing template matching by using the template generated by the template generation element 34 and the X-ray fluoroscopic radiograph.

The irradiation area projection element 36 generates the projection area denoting the therapeutic beam irradiation area by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the four-dimensional CT image data comprising a three-dimensional CT image data group consisting of the specific region in a plurality of continuous breathing phases of the subject based on the therapeutic beam irradiation area registered in the CT image data of the subject, which is generated on the therapy planning. The specific region projection element 37 generates the projection area denoting the specific-regional area by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the four-dimensional CT image data comprising a three-dimensional CT image data group consisting of the specific region in a plurality of continuous breathing phases of the subject based on the specific-regional area registered in the CT image data of the subject, which is generated on the therapy planning. The superimposition element 38 not only superimposes the projection area denoting the therapeutic beam irradiation area to the X-ray fluoroscopic radiograph, but also superimposes the projection area denoting the specific-regional area to the X-ray fluoroscopic radiograph at the position detected by the position detection element 35 based on the X-ray fluoroscopic radiograph.

The image display element 39 displays not only X-ray fluoroscopic radiograph generated by the X-ray fluoroscopic radiograph generation element 32, but also the projection area denoting the therapeutic beam irradiation area superimposed to the X-ray fluoroscopic radiograph by the superimposition element 38 and the projection area denoting the specific-regional area superimposed to the X-ray fluoroscopic radiograph by the superimposition element 38, on the display element 42. In addition, the image display element 39 displays the image including the specific region selected by the template area selection element 33 and the image obtained by superimposing the projection area denoting the specific-regional area generated by the specific region projection element 37 to the DRR image generated by the DRR image generation element 31, on the display element 42. In addition, the image display element 39 displays the X-ray fluoroscopic radiograph generated by the X-ray fluoroscopic radiograph generation element 32 and the image obtained by superimposing the projection area denoting the specific-regional area generated by the specific region projection element 37 to the DRR image generated by the DRR image generation element 31, on the display element 42.

The gating element 40 sends a therapeutic beam irradiation signal to the radiation irradiation device 90 when the projection area denoting the specific-regional area superimposed to the X-ray fluoroscopic radiograph by the superimposition element 38 are placed in the projection area denoting the therapeutic beam irradiation area superimposed to the X-ray fluoroscopic radiograph by the superimposition element 38.

Further, the control element 30 is also connected to the radiation irradiation device 90 and the therapy planning device 99 set forth above. In addition, the control element 30 and the therapy planning device 99 can be connected to each other via the radiation department information system (RIS) that is a in-house communication for the subject management system in a hospital. Now, the therapy planning device 99 makes a therapy planning prior to performing the radiation therapy. The therapy planning device 99 stores a four-dimensional CT image data comprising a group of three-dimensional DRR data including the specific region relative to a plurality of continuous breathing phases of the subject, which is acquired by performing continuously multiple times three-dimensional CT radiography of the subject using the CT radiography apparatus. Subsequently, a therapy planning for the subject is generated based on such four-dimensional CT image data and other data of the subject.

Figure 3:
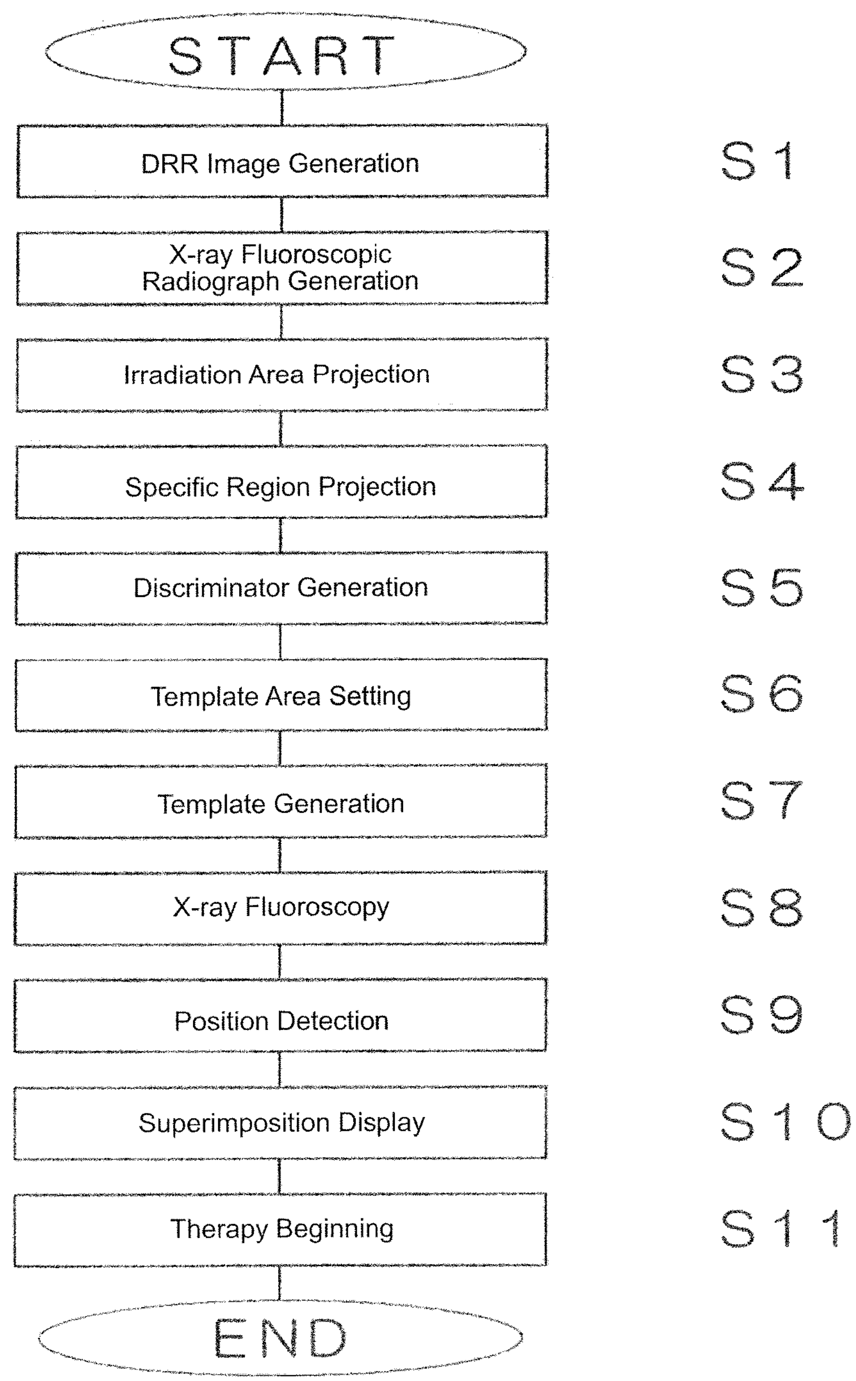
FIG. 3 is a flow-chart illustrating a tracking operation and an irradiation operation of the therapeutic beam applying the X-ray fluoroscopic apparatus according to the aspect of the present invention.

The inventor sets forth a tracking operation and an irradiation operation of the therapeutic beam applying the X-ray fluoroscopic apparatus according to the aspect of the present invention. FIG. 3 is a flow-chart illustrating a tracking operation and a therapeutic beam irradiation operation applying the X-ray fluoroscopic apparatus according to the aspect of the present invention.

When X-ray fluoroscopy is executed, referring to FIG. 2, firstly, a plurality of DRR images including the specific region is generated based on the four-dimensional CT image data generated when the therapy planning is generated by the DRR image generation element 31 (Step S1). In addition, the four-dimensional CT image data generated when the therapy planning is generated is a group of three-dimensional CT image data of the areas including the specific region, which are continuously taken with time relative to a plurality of continuous breathing phases of the subject when the therapy planning is stored in the memory storing element. The DRR image is generated by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the four-dimensional CT image data.

In such DRR generation step, a plurality of DRR images including the specific region is generated based on the CT image data of the plurality of the breathing phases including at least the breathing phase, in which the therapeutic beam is irradiated from the radiation irradiation device 90 to the subject, among the four-dimensional CT data generated when the therapy planning is generated. Such DRR images are stored in the memory storing element 41.

Subsequently, referring to FIG. 2, an X-ray fluoroscopic radiograph is generated to generate a template by the X-ray fluoroscopic radiograph generation element 32 (Step 2). At this time, the X-ray fluoroscopic radiographs of the specific region such as a tumor and so forth of a plurality of subjects are acquired by performing the X-ray fluoroscopy by applying the first X-ray radiography system comprising the first X-ray tube 11*a* and the first flat panel detector 21*a* and the second X-ray radiography system comprising the second X-ray tube 11*b* and the second flat panel detector 21*b*. Such X-ray fluoroscopic radiographs are stored in the memory storing element 41.

Subsequently, referring to FIG. 2, the irradiation area projection step is executed to generate the projection area denoting the irradiation area of the therapeutic beam by the irradiation area projection element 36 (Step S3). Specifically, the projection area denoting the therapeutic beam irradiation area is generated by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the CT image data, based on the therapeutic beam irradiation area registered on such CT image data by using the CT image data of the plurality of the breathing phases including at least the breathing (respiration) phase, in which the therapeutic beam is irradiated from the radiation irradiation device 90 to the subject, among the four-dimensional CT data which are generated on the therapy planning. The projection area denoting the therapeutic beam irradiation area is the area denoting the therapeutic beam irradiation area on the X-ray fluoroscopic radiograph and the DRR image. In addition, when the therapy planning is created, the therapeutic beam irradiation area is pre-registered in the CT image data. In such irradiation area projection step, such pre-registered therapeutic beam irradiation area is applied.

Subsequently, referring to FIG. 2, the specific area projection step is executed to generate the projection area denoting the specific-regional area by the specific region projection element 37 (Step S4). Specifically, the projection area denoting the specific-regional area is generated by performing a virtual fluoroscopic projection simulating the geometric fluoroscopy condition between the first X-ray radiography system comprising the first X-ray tube 11*a* and the first flat panel detector 21*a* and the second X-ray radiography system comprising the second X-ray tube 11*b* and the second flat panel detector 21*b* relative to the CT image data, based on the specific-regional area registered on such CT image data by using the CT image data of the plurality of the breathing phases including at least the breathing phase, in which the therapeutic beam is irradiated from the radiation irradiation device 90 to the subject, among the four-dimensional CT data which are generated on the therapy planning. The projection area denoting the specific-regional area is the area denoting the specific-regional area on the X-ray fluoroscopic radiograph and the DRR image. In addition, when the therapy planning is created, the specific-regional area is pre-registered on the CT image data. In such specific region projection step, the area of such pre-registered specific region is applied.

Subsequently, a classifier generation step (Step S5), a template area setting step (Step S6) and a template generation step (Step S7) are executed to generate the template used for the template matching to detect the position of the specific region. In addition, according to the following Embodiment, the position of the specific region is detected by applying the template matching, but the position of the specific region can be detected by classification applying the machine learning. In addition, the position of the specific region can be detected by co-applying the template matching and the machine learning together.

In the classifier generation step (Step S5), the classifier is generated to recognize the specific region by the machine learning, using a plurality of DRR images generated by the DRR image generation element 31. At this time, a large number of positive images are generated by changing parameters for generating the DRR image such as a projection coordinate and an angle relative to the four-dimensional CT image data. This time, if needed, an automatic trimming can be performed by recognizing the position and the size of the specific region in the DRR image from the position and the size of the specific region relative to the four-dimensional CT image data registered on the therapy planning. In addition, when the positive image is generated, if needed, the image following the trimming can be automatically and slightly translated, rotated, deformed, expanded, contracted, changed in contrast thereof, added in noise, enhanced in an edge to make the positive image for machine learning. The translated, the rotated, the deformed, the expanded, and the contracted image or the mix-processed image of the trimmed-image are used as the positive image so that the specific region can be tracked more exactly even when the specific region such as the tumor of the subject takes non-producible shift or deformation inside the subject relative to the four-dimensional CT image data. In addition, the contrast-changed, the noise-added and the edge-enhanced image or the mix-processed image of the trimmed-image are used as the positive image so that the specific region can be detected more exactly while canceling the difference between the DRR image and the X-ray radiograph. Subsequently, the classifier is generated by applying the positive image and the negative image following generations.

Now the negative image used together with the positive image is generated by e.g., the following method. Specifically, when the negative image is generated, the negative image is generated by performing a plurality of trimmings at the random position by-passing the specific region, i.e., the position in the background of the specific region, from the DRR image including the specific region generated by the DRR image generation element 31. In addition, when the negative image is generated, further the negative image is generated using the DRR image not-including the specific region.

For example, a deep learning represented by a convolutional neural network (CNN) can be applied to the machine learning being applied to the classifier generation step. Such convolutional neural network is one of the learning models capable of providing a highest recognition property among many methods when a pattern recognition is performed. In addition, instead of the convolutional neural network, a decision tree, a support vector machine (SVM), a boosting by such as Haar-like features can be applied to the machine learning having a superior recognition property. In addition, referring to FIG. 2, generation of the negative image and the positive image, and generation of the classifier set forth above are executed by the template area selection element 33.

Figure 4:
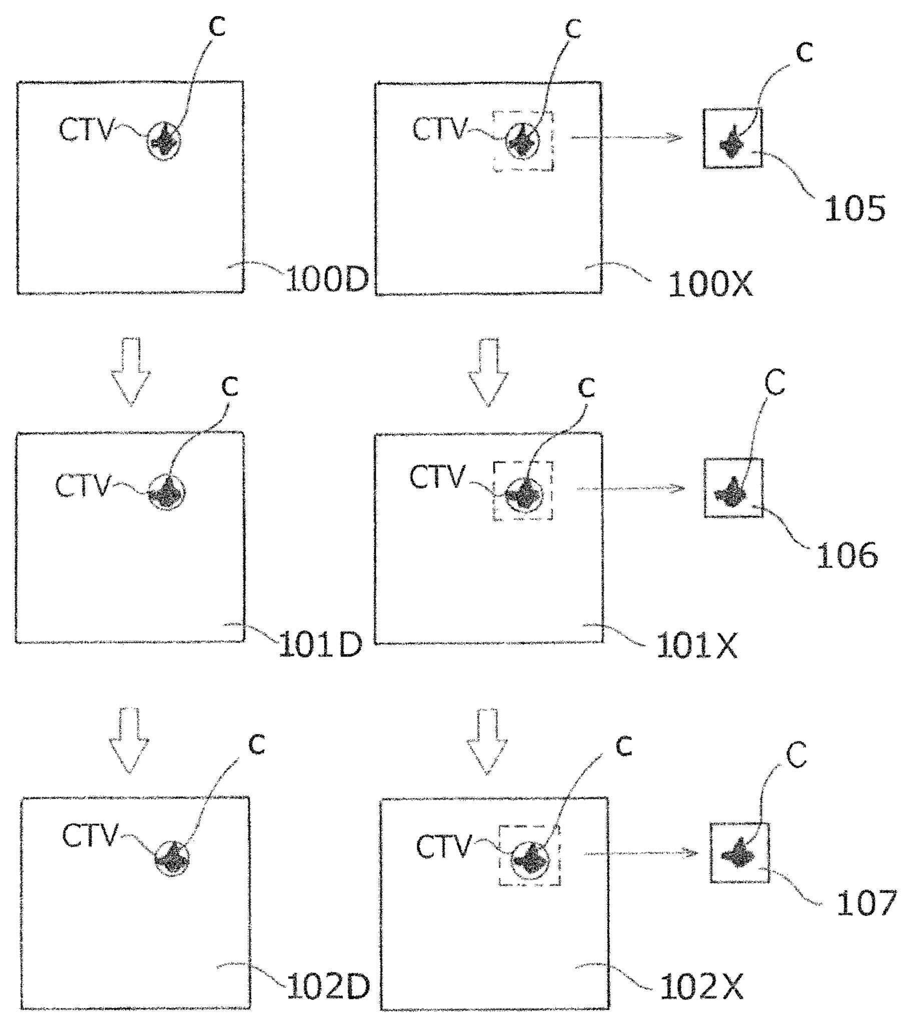
FIG. 4 is a schematic view illustrating a template area setting step.

Relative to the template area setting step (Step S6), the area including the specific region C, such as tumor and so forth, of the subject is set up as the template area. FIG. 4 is a schematic view illustrating a template area setting step. In addition, referring to FIG. 4, 100X, 101X, 102X are the X-ray fluoroscopic radiographs acquired by the X-ray fluoroscopy, and 100D, 101D, 102D are the DRR images corresponding to the respective X-ray fluoroscopic radiographs thereof.

Referring to FIG. 4, for example, three X-ray fluoroscopic radiographs 100X, 101X, 102X including the specific region C, such as a tumor and so forth, of the subject, are taken consecutively. In practical, much more images are taken depending the predetermined frame rate. Subsequently, referring to FIG. 2, the position of the specific region C is detected from such X-ray fluoroscopic radiographs 100X, 101X, 102X by performing classification using the classifier generated by the template area selection element 33 in advance. Subsequently, the area including the specific region C is set up as the template area indicated by the broken line in FIG. 4 (Step S6).

The area including the specific region C can be selected by performing consecutively the X-ray fluoroscopy and detection of the position of the specific region C. At this time, referring to FIG. 2, the image display element 39 displays the images 100D, 101D, 102D obtained by superimposing the projection area denoting the specific-regional area C generated by the specific region projection element 37 to the DRR image including the specific region C generated by the DRR image generation element 31, in parallel. The operator can make a decision whether or not the position of the selected specific region C comparing such X-ray fluoroscopic radiographs 100X, 101X, 102X and the DRR images 100D, 101D, 102D is appropriate by eyes. If inappropriate due to shift of the position of the specific region C and so forth, the operator can correct such shift.

In addition, e.g., a clinical target volume (CTV) and so forth can be adopted as the specific-regional area C. Such terms are registered in the therapy planning, so that the area projected on the DRR images 100D, 101D, 102D can be calculated from the geometric condition of the X-ray radiographic apparatus. A profile of such projected area is superimposed to the DRR images 100D, 101D, 102D and displayed.

In addition, referring to FIG. 2, relative to the position of the specific region C selected in the X-ray fluoroscopic radiographs 100X, 101X, 102X, the image display element 39 superimposes the projection area denoting the specific-regional area C generated by the specific region projection element 37 to the X-ray fluoroscopic radiographs 100X, 101X, 102X and displays therefor.

Referring to FIG. 4, the projection area denoting the specific region, which are superimposed to the X-ray fluoroscopic radiographs 100X, 101X, 102X and the DRR images 100D, 101D, 102D and displayed, are indicated by the sign CTV. In addition, referring to FIG. 4, for convenience sake to explain, the CTV is illustrated as a circle, but in practical, the shape of the CTV resembles the shape of the specific region C of the subject.

In addition, relative to the DRR images 100D, 101D, 102D and the specific-regional area C, the closest phase to phase-correspond to the X-ray fluoroscopic radiographs 100X, 101X, 102X and the phase is displayed. When such phase is synchronized, for example, a signal from outside instruments monitoring the movement between breast and berry of the subject by a camera and a pressure sensor and so forth can be applied. In addition, the closest phase can be selected due to the image matching (coincidence) degree, or the operator can select manually.

In addition, the X-ray fluoroscopic radiographs 100X, 101X, 102X and the DRR images 100D, 101D, 102D are not required to be displayed at the same time and in parallel and can be displayed alternatively. In fact, it can be displayed as the operator could decide whether or not the position of the specific region C is appropriate.

In the template generation step (Step S7), a trimming is executed relative to the area including the specific region C selected in the X-ray fluoroscopic radiographs 100X, 101X, 102X. Referring to FIG. 4, the respective images 105, 106, 107 following the trimming are selected as a template applied to multi template matchings. Such templates are stored in the memory storing element 41 referring to FIG. 2. In addition, such images 105, 106, 107 can be used as the positive images for the machine learning in the following therapy and later. Similarly, the respective X-ray fluoroscopic radiographs 100X, 101X, 102X can be used as the negative images for the machine learning in the following therapy and later while by-passing the selected templates 105, 106, 107.

As set forth above, in the processes executing the classifier generation step (Step S5), the template area setting step (Step S6) and the template generation step (Step S7), the DRR images 100D, 101D, 102D superimposing the projection area denoting the area of the specific region C generated by the specific region projection element 37 are displayed together with the X-ray fluoroscopic radiographs 100X, 101X, 102X superimposing the projection area denoting the area of the specific region C generated by the specific region projection element 37. The operator can compare such X-ray fluoroscopic radiographs 100X, 101X, 102X and the DRR images 100D, 101D, 102D by eyes. The operator can make exactly a decision whether or not the position of the selected specific region C is appropriate even when the specific region C in the X-ray fluoroscopic radiographs 100X, 101X, 102X is poorly recognizable by eyes.

Subsequently, the classifier generation step (Step S5), the template area setting step (Step S6) and the template generation step (Step S7), set forth above, can be automatically executed by machine learning. Consequently, not only the subject is not temporally-constrained as when the operator manually selects the template right before the radiation therapy, but also the throughput for the radiation therapy can be increased. The real-time selection due to the machine learning is not mandatory because of confirmation by eyes and a high cost algorithms focusing on the accuracy of the position is feasible.

In addition, according to the aspect of the Embodiment as set forth above, the template area is selected by executing the machine learning relative to the X-ray fluoroscopic radiographs 100X, 101X, 102X generated by the X-ray fluoroscopic radiograph generation element 32, but instead of X-ray fluoroscopic radiographs 100X, 101X, 102X, the template area is selected by executing the machine learning relative to the DRR images 100D, 101D, 102D including the specific region generated by the DRR image generation element 31 based on the four-dimensional CT image data.

In addition, according to the aspect of the Embodiment as set forth above, the template area is set up by the machine learning, but the operator can trim the specific region C from the X-ray fluoroscopic radiographs 100X, 101X, 102X. In addition, instead of the trimming by the operator, an automatic trimming can be executed by acquiring the projection position of the specific region C of each phase from the position of the specific region C in the four-dimensional CT data applied to the therapy planning and recognizing the position of the specific region C from the corresponding relationship between the X-ray fluoroscopic radiographs 100X, 101X, 102X and the four-dimensional CT data. Further, the operator acquires the approximate position of the specific region C by utilizing the four-dimensional data and can correct the position thereof.

Once the above preparation processes complete, the subject is reloaded on the examination table 29 and the X-ray fluoroscopy using the X-ray fluoroscopic apparatus according to the present invention is performed to execute the tracking. Such X-ray fluoroscopy is performed at the predetermined frame rate, e.g., approximately 30 fps (frame per second). Subsequently, relative to the plurality of X-ray fluoroscopic radiographs acquired at the predetermined frame rate, the position of the specific region C is detected (Step S9) by performing multi template matchings applying a plurality of templates that are generated in the template generation step (Step S7) and stored in the memory storing element 41, referring to FIG. 2.

According to the multi template matchings, for example, the X-ray fluoroscopic radiograph is searched and the image of the search area is compared with a plurality of template images stored in the memory storing element 41 to obtain similarity thereof and the position having the similarity degree higher than the predetermined threshold value is determined as the position of the specific region C. The detection of the position of the specific region C according to the template matching is performed at the timing coinciding with the frame rate.

Figure 5:
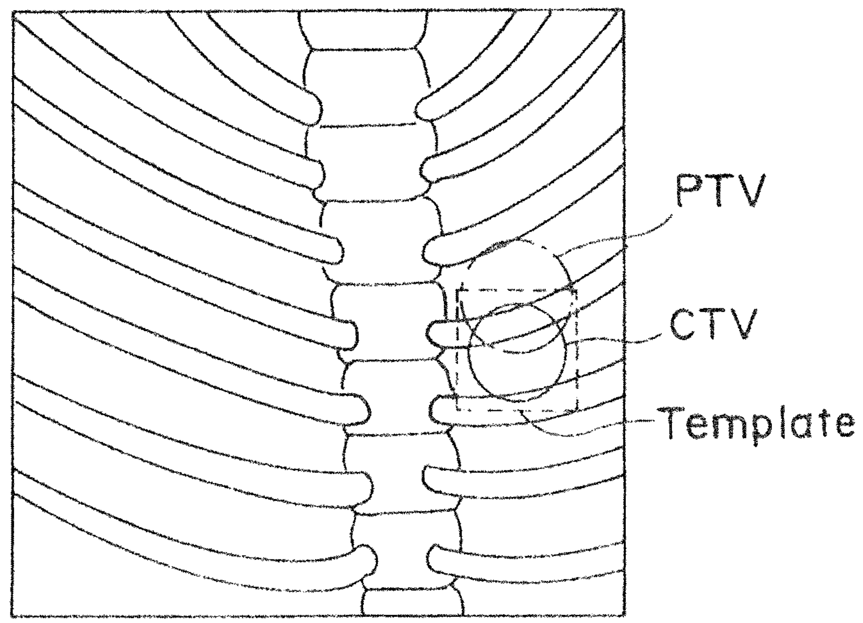
FIG. 5 is a schematic view illustrating an X-ray fluoroscopic radiograph.
Figure 6:
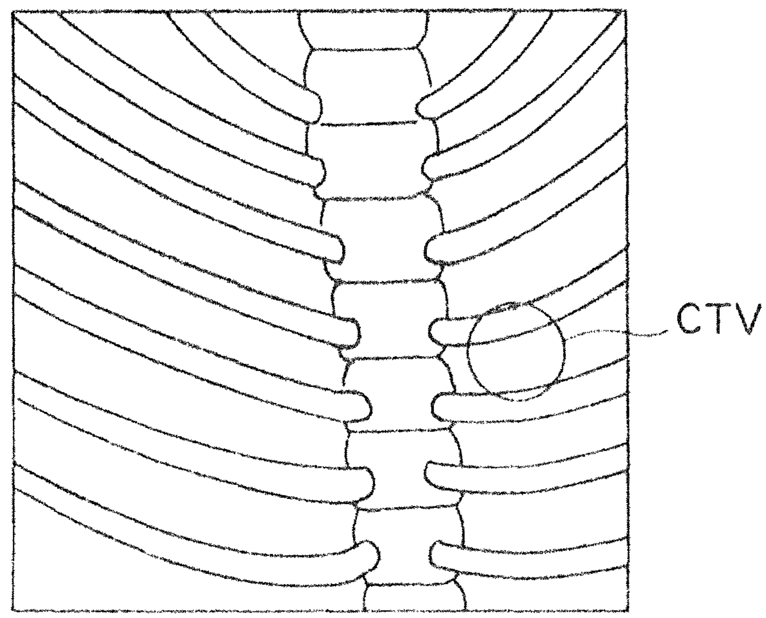
FIG. 6 is a schematic view illustrating a DRR image.

FIG. 5 is a schematic view illustrating an X-ray fluoroscopic radiograph at this time. FIG. 6 is a schematic view illustrating the DRR image having the same phase as the X-ray fluoroscopic radiograph referring to FIG. 5.

When such template matching is performed, the operator confirms whether or not the tracking is correctly being performed by eyes before the therapeutic beam irradiation.

At this time, referring to FIG. 5, the image display element 39 referring to FIG. 2 displays the projection area denoting the therapeutic beam irradiation area relative to the X-ray fluoroscopic radiograph on the display element 42

(Step S10). Such irradiation area is e.g., a planning target volume (PTV). Such a planning target volume (PTV) is registered in the therapy planning. Subsequently, referring to FIG. 2, the irradiation area projection element 36 calculates the area to be projected on the X-ray radiograph by performing a virtual fluoroscopic projection simulating the geometric fluoroscopy condition between the first X-ray radiography system comprising the first X-ray tube 11a and the first flat panel detector 21a and the second X-ray radiography system comprising the second X-ray tube 11b and the second flat panel detector 21b. Subsequently, the superimposition element 38 superimposes such area on the X-ray fluoroscopic radiograph. The image display element 39 displays the profile of the projection area superimposed on the X-ray fluoroscopic radiograph together with the X-ray fluoroscopic radiograph on the display element 42 referring to FIG. 2. Such projection area is indicated by the dashed-line signed as PTV referring to FIG. 5. In addition, in practice, the projection area PTV is displayed as a specific colored line relative to X-ray fluoroscopic radiograph displayed on the display element 42.

In addition, similarly, referring to FIG. 5, the image display element 39 referring to FIG. 2 displays the projection area denoting the specific-regional area C relative to the X-ray fluoroscopic radiograph on the display element 42 (Step S10). Such specific-regional area C is, e.g., the clinical target volume (CTV) set forth above. Such a clinical target volume (CTV) is registered in the therapy planning as set forth above. Subsequently, referring to FIG. 2, the specific region area projection element 37 calculates the area to be projected on the X-ray radiograph by performing a virtual fluoroscopic projection simulating the geometric fluoroscopy condition between the first X-ray radiography system comprising the first X-ray tube 11a and the first flat panel detector 21a and the second X-ray radiography system comprising the second X-ray tube 11b and the second flat panel detector 21b. The superimposition element 38 superimposes such area to the position of the specific region detected by the position detection element 35 based on the X-ray fluoroscopic radiograph relative to the X-ray fluoroscopic radiograph. The image display element 39 displays the profile of the projection area superimposed on the X-ray fluoroscopic radiograph together with the X-ray fluoroscopic radiograph on the display element 42 referring to FIG. 2. Such projection area is indicated by the solid-line signed as CTV referring to FIG. 5. In addition, in practice, the projection area CTV is displayed as a different, specific colored line from PTV relative to X-ray fluoroscopic radiograph displayed on the display element 42.

In addition, referring to FIG. 5, the rectangular area indicating the template area is indicated by the broken line signed as Template. In practice, the area Template is displayed as a different, specific colored line from CTV and PTV relative to X-ray fluoroscopic radiograph displayed on the display element 42.

In addition, referring to FIG. 6, the image display element 39 displays the projection area CTV denoting the therapeutic beam irradiation area relative to the DRR image generated by the DRR image generation element 31 on the display element 42 as well as the X-ray fluoroscopic radiograph. The operator can confirm whether or not the tracking of the specific region C of the subject is being performed appropriately by comparing with the X-ray fluoroscopic radiograph and the DRR image displayed on the display element 42.

In addition, referring to FIG. 5, FIG. 8, for convenience sake to explain, the CTV and the PTV are depicted as a circle, but in practical, the shape of the CTV and the PTV resemble the shape of the specific region C of the subject.

Subsequently, the radiation therapy begins (Step S11). At this time, referring to FIG. 2, the gating element 40 sends a therapeutic beam irradiation signal to the radiation irradiation device 90 when the projection area CTV denoting the area of the specific region C superimposed to the specific region C of the subject in the X-ray fluoroscopic radiograph by the superimposition element 38 are placed in the projection area PTV denoting the therapeutic beam irradiation area superimposed to the X-ray fluoroscopic radiograph by the superimposition element 38. Consequently, the gating of the radiation irradiation device 90 is turned ON, and the head 93 of the radiation irradiation device 90 irradiates the therapeutic beam to the subject. Such detection of the position of the specific region C and the irradiation of the therapeutic beam are repeated until the therapy completes.

The operator can confirm whether or not the tracking of the specific region C of the subject is being performed appropriately by comparing with the X-ray fluoroscopic radiograph and the DRR image displayed on the display element 42. At this time, when the projection area CTV denoting the specific-regional area C is place in the projection area PTV denoting the therapeutic beam irradiation area, a lamp can be lighted or sounds can be emitted to notify the operator such incident.

In addition, the phase of the DRR image generated by the DRR image generation element 31 and the phase of the X-ray fluoroscopic radiograph (i.e., phase of the specific region C) generated by the X-ray fluoroscopic radiograph generation element 32 may not be always matched to each other. Accordingly, the closest phase can be selected by corresponding to both phases. At this time, the phase synchronization can apply a signal from outside instruments monitoring the movement between breast and berry of the subject by a camera and a pressure sensor and so forth. In addition, the closest phase can be selected due to the image matching (coincidence) degree.

In addition, according to the aspect of the Embodiment as set forth above, the position of the specific region C of the subject is being tracked using a plurality of the templates, but the position of the specific region C can be tracked by classification due to the machine learning.

REFERENCE OF SIGNS

11a First X-ray tube
11b Second X-ray tube
21a First flat panel detector
21b Second flat panel detector
29 Examination table
30 Control element
31 DRR image generation element
32 X-ray fluoroscopic radiograph generation element
33 Template area selection element
34 Template generation element
35 Position detection element
36 Irradiation area projection element
37 Specific region projection element
38 Superimposition element
39 Image display element
40 Gating element
41 Memory storing element
42 Display element
90 Radiation irradiation device
99 Therapy planning device
C Specific region As used herein, a computer related system comprises an input device for receiving data, an output device for outputting data in tangible form (e.g. printing or displaying on a computer screen, transmitting values or data or pixels of some kind, sending instruction impulses etc.), a memory for storing data as well as computer code of any necessary form for component operation and database or communication operation, and a microprocessor for executing computer code wherein said computer code resident in said memory will physically cause said microprocessor to read-in, process and output said processed data via said output device.

It will be further understood by those of skill in the art that the apparatus and devices and the elements herein, without limitation, and including the sub components such as operational structures, circuits, communication pathways, and related elements, control elements of all kinds, display circuits, elements, and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray Fluoroscopic diagnostic devices, computer and operational controls and technologies of radiographic devices and all their sub components, X-ray emitters/tubes, display elements such as display screens or monitors, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module may reside in Random Access Memory (RAM), flash memory. Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic apparatus, that collects an X-ray fluoroscopic radiograph including a specific region of a subject and detects a position of the specific region, and sends a therapeutic beam irradiation signal to a radiation irradiation device while tracking a movement of said specific region, said X-ray fluoroscopic apparatus, further comprising:

an X-ray tube;

an X-ray detector that detects an X-ray that is irradiated from said X-ray tube and transmits through said subject;

an irradiation area projection element that generates a projection area denoting a therapeutic beam irradiation area by performing a virtual fluoroscopic projection simulating a geometric fluoroscopic condition between said X-ray tube and said X-ray detector relative to an initial set of CT image data based on said therapeutic beam irradiation area registered in said CT image data of said subject generated when an initial therapy planning is created;

a specific region projection element that generates a specific projection area denoting a specific regional area by performing a virtual fluoroscopic projection simulating a geometric fluoroscopic condition between said X-ray tube and said X-ray detector relative to said initial set of CT image data based on the specific region registered on said CT image data of said subject generated when said therapy planning is created;

a superimposition element that both superimposes the projection area denoting said therapeutic beam irradiation area onto said X-ray fluoroscopic radiograph, and superimposes the specific projection area denoting said specific-regional area to said X-ray fluoroscopic radiograph at said specific-regional position detected based on said X-ray fluoroscopic radiograph; and a gating element that sends the therapeutic beam irradiation signal to the radiation irradiation apparatus when the projection area denoting the specific-regional area superimposed onto the X-ray fluoroscopic radiograph by said superimposition element are placed in the projection area denoting the therapeutic beam irradiation area superimposed to the X-ray fluoroscopic radiograph by the superimposition element.

2. The X-ray fluoroscopic apparatus, according to claim 1, further comprising:

an image display element that displays the X-ray fluoroscopic radiograph and the projection area denoting said therapeutic beam irradiation area superimposed on said X-ray fluoroscopic radiograph by said superimposition element and the projection area denoting said specific-regional area superimposed to said X-ray fluoroscopic radiograph by said superimposition element.

3. The X-ray fluoroscopic apparatus, according to claim 1, further comprising:

a template area selection element that selects an area including said specific region from said X-ray fluoroscopic radiograph;

a template generation element that generates a template indicating said specific region from the area including said specific region selected by said template area selection element; and a position detection element that detects a position of said specific region relative to said fluoroscopic radiograph by performing template matching by using the template generated by using said X-ray fluoroscopic radiograph and said template generation element.

4. The X-ray fluoroscopic apparatus, according to claim 3, wherein:

said template area selection element selects an area including said specific region from said X-ray fluoroscopic radiograph by a DRR (digital reconstructed radiography) image generated by one of a step of:

performing the virtual fluoroscopic projection simulating a geometric fluoroscopic condition between said X-ray tube and said X-ray detector relative to said CT image data; and machine learning learned using an X-ray fluoroscopic radiograph obtained by an X-ray fluoroscopy of said subject in advance.

5. The X-ray fluoroscopic apparatus, according to claim 4, wherein:

said machine learning that is one selected from the group consisting of:

a support vector machine, a decision tree, a boosting and a neural network.

6. The X-ray fluoroscopic apparatus, according to claim 3, further comprising:

a DRR image generation element that generates a DRR image including said specific region by performing a virtual fluoroscopic projection simulating a geometric fluoroscopic condition between said X-ray tube and said X-ray detector relative to CT image data of said subject generated when a therapy planning is created; and an image display element that displays an image including said specific region selected by said template area selection element and an image obtained by superimposing a projection area denoting said specific region generated by said specific region projection element to a DRR image generated by said DRR image generation element.

7. The X-ray fluoroscopic apparatus, according to claim 1, further comprising:

a DRR image generation element that generates a DRR image including said specific region by performing a virtual fluoroscopic projection simulating a geometric fluoroscopic condition between said X-ray tube and said X-ray detector relative to CT image data of said subject generated when said initial therapy planning is created; and an image display element that displays said X-ray fluoroscopic radiograph and an image obtained by superimposing a projection area denoting said specific region generated by said specific region projection element to a DRR image generated by said DRR image generation element.

8. The X-ray fluoroscopic apparatus, according to claim 6, wherein:

said CT image data is a four-dimensional CT image data, further comprising:

a group of three-dimensional CT image data including said specific region relative to a plurality of continuous breathing phases of said subject; and said DRR image generation element generates a DRR image including said specific region based on CT image data of phases in association with said X-ray fluoroscopic radiograph.

9. The X-ray fluoroscopic apparatus, according to claim 1, further comprising:

said CT image data is a four-dimensional CT image data, further comprising:

a group of three-dimensional CT image data including said specific region relative to a plurality of continuous breathing phases of said subject; and said specific region projection element generates a projection area denoting said specific region based on CT image data of phases in association with said X-ray fluoroscopic radiograph.

10. An x-ray fluoroscopic apparatus, comprising:

an X-ray tube;

an X-ray detector that detects an X-ray that is irradiated from said X-ray tube and transmits through a subject; wherein:

said X-ray fluoroscopic apparatus collects an X-ray fluoroscopic radiograph including a specific region of said subject and detects a position of the specific region, and sends a therapeutic beam irradiation signal to a radiation irradiation device while tracking a movement of said specific region;

a specific region projection element that generates a projection area denoting said specific-regional area by performing a virtual fluoroscopic projection simulating a geometric fluoroscopic condition between said X-ray tube and said X-ray detector relative to an initial set of CT image data of said subject based on said specific region registered on said CT image data of said subject generated when an initial therapy planning is created;

a DRR image generation element that generates a DRR image including said specific region by performing a virtual fluoroscopic projection simulating a geometric fluoroscopic condition between said X-ray tube and said X-ray detector relative to CT image data of said subject generated when said initial therapy planning is created;

a template area selection element that selects an area including said specific region from said X-ray fluoroscopic radiograph;

an image display element that displays an image of an area including said specific region in said X-ray fluoroscopic radiograph selected by said template area selection element, and an image obtained by superimposing a projection area denoting said specific region generated by said specific region projection element to a DRR image generated by said DRR image generation element;

a template generation element that generates a template indicating said specific region from an area including said specific region selected by said template area selection element; and a position detection element that detects a position of said specific region relative to said fluoroscopic radiograph by performing template matching by using said X-ray fluoroscopic radiograph and a template generated by said template generation element.

11. The X-ray fluoroscopic apparatus, according to claim 10, wherein:

said template area selection element selects a DRR image generated by a step of performing a virtual fluoroscopic projection simulating a geometric fluoroscopic condition between said X-ray tube and said X-ray detector relative to said CT image data, or selecting an area including said specific region from said X-ray fluoroscopic radiograph by machine learning learned using an X-ray fluoroscopic radiograph obtained by an initial X-ray fluoroscopy of said subject in advance.

12. The X-ray fluoroscopic apparatus, according to claim 11, wherein:

said machine learning that is one selected from the group consisting of:

a support vector machine, a decision tree, a boosting and a neural network.

* * * * *